(12) United States Patent
Ikeda

(10) Patent No.: US 6,480,570 B1
(45) Date of Patent: *Nov. 12, 2002

(54) X-RAY IMAGE DISPLAY APPARATUS

(75) Inventor: Shigeyuki Ikeda, Kashiwa (JP)

(73) Assignee: Hitachi Medical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 60 days.

(21) Appl. No.: 08/796,445

(22) Filed: Feb. 10, 1997

Related U.S. Application Data

(63) Continuation of application No. 08/398,808, filed on Mar. 6, 1995.

(30) Foreign Application Priority Data

Mar. 11, 1994 (JP) .............................. 6-066514

(51) Int. Cl.⁷ ................................................ H05G 1/64
(52) U.S. Cl. ...................... 378/98.7; 378/98.2
(58) Field of Search ................ 378/98.7, 98.2, 378/156, 150, 151

(56) References Cited

U.S. PATENT DOCUMENTS 5,278,887 A * 1/1994 Chiu et al. ................ 378/98.2
5,287,396 A * 2/1994 Stegehuis ................ 378/98.2

OTHER PUBLICATIONS

"Christensens Physics of Diagnostic Radiology", Curry 1990 p 93–95.*
Specification, X–ray Adjustable Collimator System, Model ZU–L5F, Japanese and English editions, Hitachi Medical Corporation, Tokyo, 1993 (Japanese edition), 1994 (English edition).

* cited by examiner

Primary Examiner—Craig E. Church
(74) Attorney, Agent, or Firm—Antonelli, Terry, Stout & Kraus, LLP.

(57) ABSTRACT

An X-ray image display apparatus for exposing a subject to an X-ray to obtain an X-ray image of the subject, picking up the X-ray image, converting it to a digital video signal, performing necessary signal processing on the digital video signal in an image processor to obtain X-ray image data, and displaying, on a display device, an image of a display area included in the X-ray image and specified by an input device includes a display area detector for detecting display area data representing the specified display area, and a control circuit for outputting a control signal to control a collimator drive circuit and/or a filter drive circuit on the basis of the display area data detected by the display area detector and x-ray image data supplied from the image processor, thereby controlling the position of a collimator and/or a filter so as to display the image of the display area optimally.

17 Claims, 9 Drawing Sheets

X-RAY IMAGE DISPLAY APPARATUS

CROSS-REFERENCE TO RELATED APPLICATION

This is a continuation of application Ser. No. 08/398,808 filed on Mar. 6, 1995.

BACKGROUND OF THE INVENTION

The present invention relates to an X-ray image display apparatus for exposing a subject to an X-ray and thereby performing fluoroscopy and radiography on a subject region, and in particular to an X-ray image display apparatus in which a compensation filter and a collimator can be controlled so as to display an image satisfactorily on an image display device.

As shown in FIG. 1, a conventional X-ray image display apparatus of this kind includes a bed 2 for placing a subject 1 thereon, an X-ray tube 3 for exposing the subject 1 to an X-ray, an X-ray detector 4 disposed on the opposite side of the bed 2 from the X-ray tube 3 to convert an image of the X-ray transmitted through the subject 1 to a visible light image, a support 5 for supporting the X-ray tube 3 and the X-ray detector 4, a television camera 6 for scanning the visible light image supplied from the X-ray detector 4 and outputting a video signal, an A/D converter 7 for converting the video signal supplied from the television camera 6 to a digital signal, a display processor 8 for processing the digital signal supplied from the A/D converter 7 and converting the processed image data to a video signal, an image display device 9 for displaying the video signal inputted from the display processor 8 as an image, a compensation filter 10 disposed between the X-ray tube 3 and the subject 1 to partially an X-ray exposure dose, a filter control circuit 11 for manually adjusting the position of the compensation filter 10, a collimator 12 disposed on an output face of the X-ray tube 3 to partially interrupt the X-ray, and a collimator control circuit 13 for manually adjusting the collimator 12. The display processor 8 includes an image processor 14 for conducting processing such as frequency emphasis and subtraction on the digital signal supplied from the A/D converter 7, and a display circuit 15 for converting image data supplied from the image processor 14 to a video signal. In FIG. 1, numeral 16 denotes an X-ray controller for controlling the operation of the X-ray tube 3, and numeral 17 denotes a support controller for controlling driving of the bed 2 and the support 5.

In such an X-ray image display apparatus, an unnecessary part near the X-ray emitted from the X-ray tube 3 or a part where severe halation has occurred is interrupted by manually adjusting the collimator control circuit 13 while observing the image displayed on the image display device 9. As for a part having brightness close to that of halation, the brightness is lowered by adjusting the filter control circuit 11.

As an improvement to the conventional technique as shown in FIG. 1, a circuit for automatically controlling the filter control circuit 11 and the collimator control circuit 13 by using image data generated by the display processor 8 may occur to those skilled in the art. The circuit shown in FIG. 2 is a development of the conventional technique, and corresponds to an intermediate technique located between the conventional technique and the present invention.

In the X-ray image display apparatus shown in FIG. 2 with such an improvement added thereto, automatic control of the compensation filter 10 for removing unnecessary parts of the X-ray emitted from the X-ray tube 3 is exercised on the basis of a suitable control position calculated by the filter control circuit 11 by using image data taken in from the image processor included in the display processor 8. Representive examples of such calculation and control will now be described by referring to FIG. 3. FIG. 3 shows an output image region of the X-ray detector 4 including an X-ray image intensifier. The output image region is included in the scanning region of the television camera 6. The output image region is circular in shape. Therefore, the inside of a circle denoted by numeral 4 becomes an effective image region. The circular region is divided into a plurality of region blocks a, b, c, . . . , u. A representative value included in each region block is compared with a reference value. On the basis thereof, the filter control circuit 11 makes a calculation to determine whether the compensation filter 10 should be used or not. In general, it is desirable to conduct weighting in the central part and the peripheral part in the circular region and exercise control so as to form a satisfactory image in the central part. In case the X-ray passes outside the subject 1, i.e., the X-ray is directly incident upon the peripheral part of the X-ray detector 4, or in case a large quantity of contrast medium gathers in one place in subject 1 and hence the place can be judged to be a dark portion, it is also possible to exercise such control as to disregard the representative value of the region block of that part. A control signal based upon calculation in the filter control circuit 11 is sent to the compensation filter 10 to control the position of the compensation filter 10. By exercising such feedback control, a satisfactory image having reduced halation is obtained in fluoroscopy of a target part of the subject 1.

In recent years, advancements in image processing techniques have made it possible to expand and display moving pictures in real time and perform filtering on images in a video processing circuit. Expansion display been conventionally performed by changing the size of the image intensifier functioning as the X-ray detector 4. In angiography of the subject 1, however, a catheter and a guide wire have become very thin. In case expansion is performed only by stepwise changing the pickup range of the display screen of the image intensifier, the display area becomes narrower as the expansion ratio is increased. When the image is expanded, therefore, the catheter or wire might depart from the display range and be lost. Or even if the subject moves or the bed is slightly moved during display of an expanded image, the catheter or wire might depart from the display range and be lost. Thus, such expansion display has become uncapable of coping with such disadvantages. Therefore, expansion display using the display circuit 15 shown in FIG. 2 and digital processing has been put to use. In this case, an arbitrary area can be expanded or compressed at an arbitrary magnification owing to digital processing. In FIG. 4, the picked-up image area is represented by a square region E. FIG. 5 shows the display image area of the image display device 9. If, as an example, region blocks e, f, g, j, k, 1, o, p and q in the area included in the square region E shown in FIG. 4 are expanded by the display circuit 15, only the portion including the region blocks e, f, g, j, k, l, o, p and q is expanded and displayed on the screen of the image display device 9 as shown in FIG. 5. By using the image thus expanded and displayed, even a fine cathether can be easily manipulated.

In case expansion display using the display circuit 15 and digital processing is made in the image display in such an X-ray image diagnostic apparatus, the image in the area included in the square region E shown in FIG. 4 is taken in and the compensation filter 10 is controlled by the filter control circuit 11 by using representative values of respective region blocks e, f, g, j, k, l, o, p and q. Therefore, a satisfactory image is obtained as the entire image in the region 4. As for the expanded and displayed image portion shown in FIG. 5, however, a satisfactory display image is not obtained. The peripheral region shown in FIG. 4 is an area which is not observed. In the portion including the region blocks a, b, c, h, m, r, d, i, n, s, t and u, the subject 1 is thus subjected to unnecessary X-ray exposure. Therefore, the subject 1 is subjected to unnecessary exposure to the X-ray.

SUMMARY OF THE INVENTION

An object of the present invention is to provide an X-ray image display apparatus in which the position of a compensation filter or a collimator is controlled on the basis of display image data so as to display an image most satisfactorily.

Another object of the present invention is to provide an X-ray image display apparatus in which the position of a collimator is controlled on the basis of display image data so as to reduce exposure of a portion of the subject which is not displayed on the image to the X-ray.

In X-ray image display apparatuses, an X-ray image obtained by an X-ray detector is picked up by a television camera and the X-ray image thus picked up is subjected to image processing in a display processor and displayed on an image display device. However, the image actually displayed on the image display device is different from the X-ray image obtained by the X-ray detector. Even if an adjustment is made so as to optimize the X-ray image, therefore, it does not necessarily follow that the image displayed on the image 10 display device is optimized.

In accordance with the present invention, therefore, the apparatus includes a display area detector for detecting, on the basis of display image data processed by a display processor, a display area included in an X-ray image obtained by an X-ray detector and displayed on an image display device, and the position of a compensation filter or a collimator is controlled so as to optimize the X-ray image in the display area detected by the display area detector.

In accordance with another aspect of the present invention, the position of the collimator is controlled so as to expose only the part of the subject associated with the display area to the X-ray without exposing parts of the subject other than the display area detected by the display area detector to the X-ray.

In accordance with still another aspect of the present invention, a compensation filter for decreasing X-ray exposure dose is inserted for a portion brought to a halation state or a near-halation state and included in a display area detected by the display area detector, and the position of the compensation filter is controlled so as to make an image displayed on an image display device satisfactory. In particular, the X-ray directed to portions other than the display area is interrupted by a collimator to prevent the subject from being exposed to the X-ray. When an especially severe halation portion included in the display area cannot be sufficiently reduced by a compensation filter alone, the X-ray directed to that portion may be interrupted by inserting a collimator.

Operation of the X-ray image display apparatus thus configured will now be described. An image signal supplied from a display processor is inputted to a display area detector connected to the display processor. An image display area is detected by the display area detector. An image signal of the detected display area is sent to a filter control circuit. The compensation filter or collimator of the X-ray tube is controlled on the basis of the image signal of the display area by operation of this filter control circuit. As a result, the compensation filter or collimator can be controlled optimally.

DESCRIPTION OF THE PREFERRED EMBODIMENTS

Hereafter, embodiments of the present invention will be described in detail by referring to the attached drawings.

Figure 1:
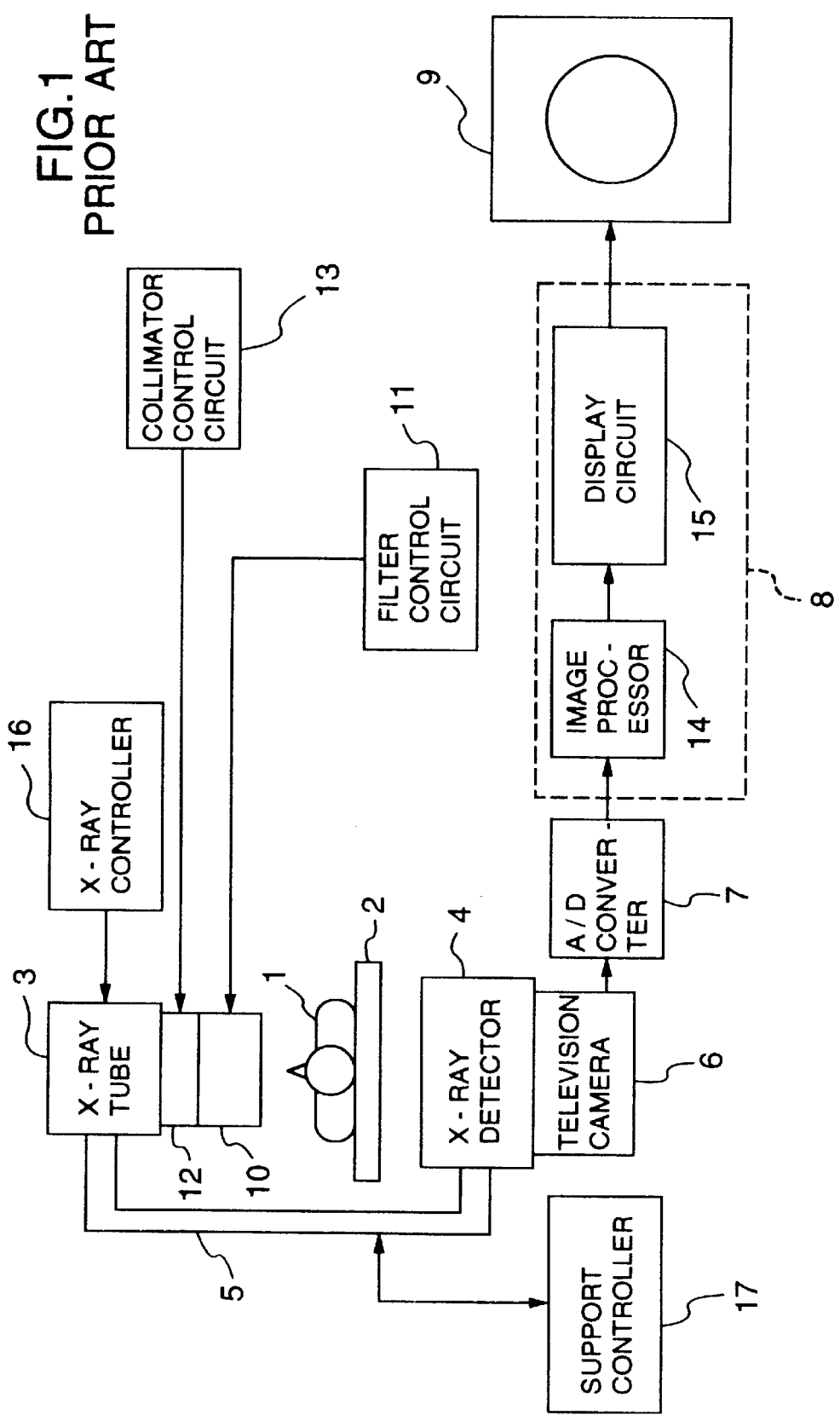
FIG. 1 is a block diagram showing a conventional X-ray image display apparatus.
Figure 2:
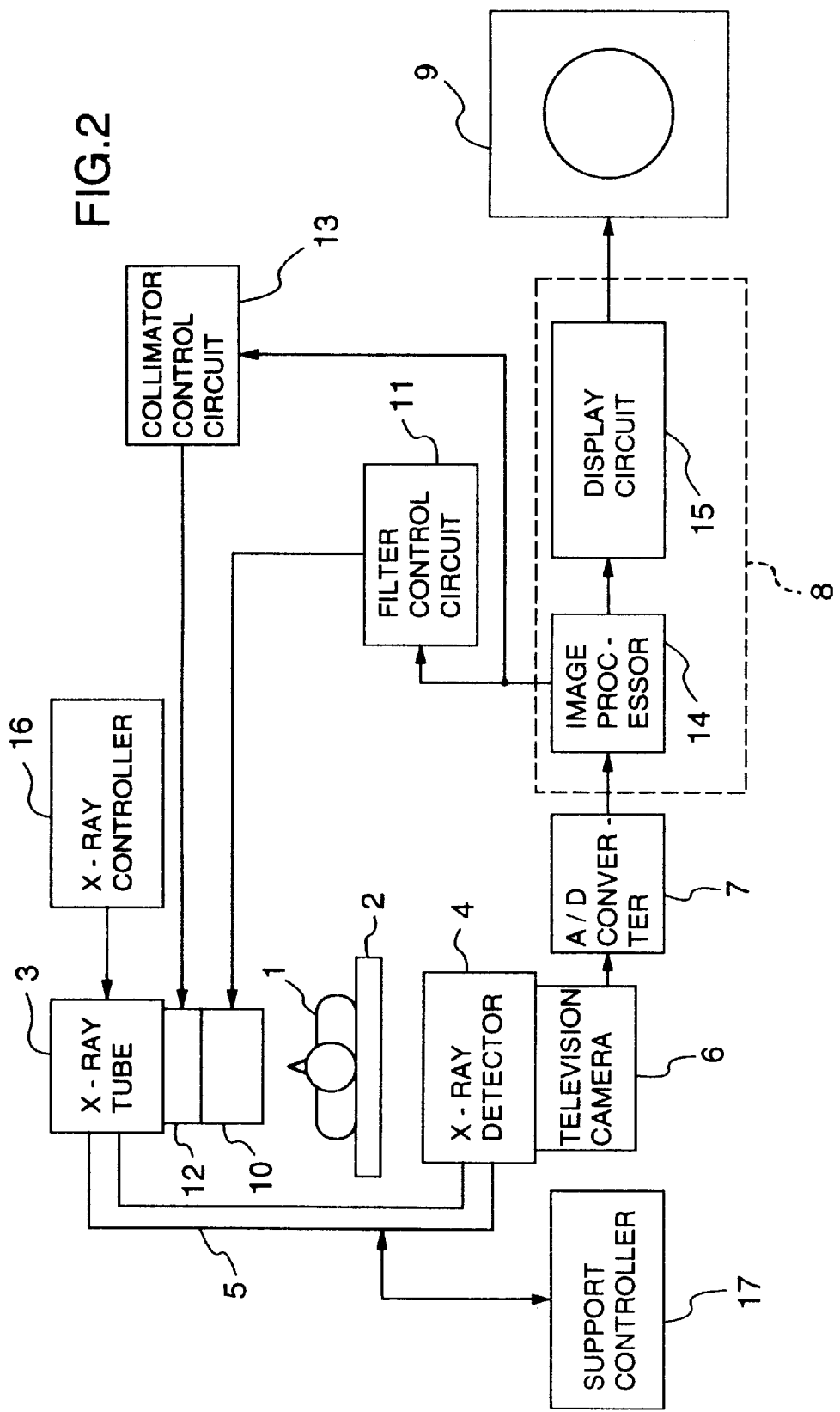
FIG. 2 is a block diagram showing an X-ray image display apparatus obtained by partially improving the apparatus illustrated in FIG. 1 and situated midway in technical level between the conventional technique and the present invention.
Figure 3:
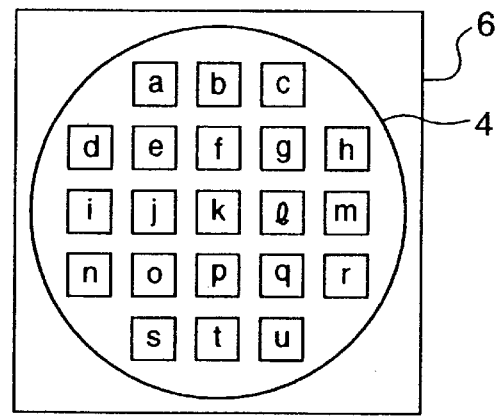
FIG. 3 is a diagram for explaining an example of feature value extraction of an image picked up in the apparatus shown in FIG. 2.
Figure 6:
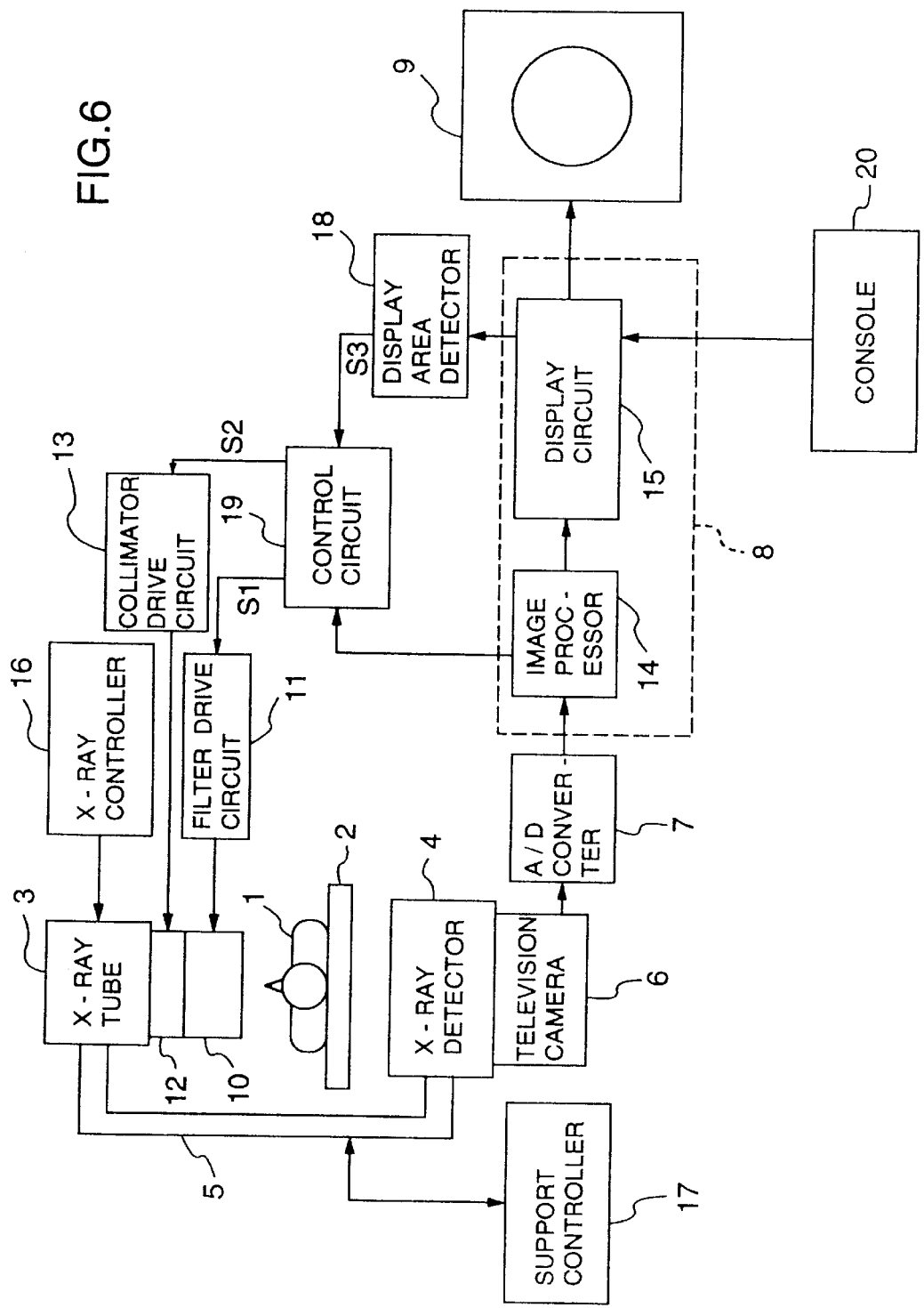
FIG. 6 is a block diagram showing an embodiment of the present invention.

FIG. 6 is a block diagram showing an embodiment of an X-ray image display apparatus according to the present invention. Components corresponding to those of FIG. 2 are denoted by like numerals. This X-ray image display apparatus is used to expose a subject 1 to the X-ray and perform fluoroscopy and radiography on a target part. As shown in FIG. 6, the X-ray image display apparatus includes a bed 2, a support 5 for supporting an X-ray tube 3 and an X-ray detector 4, a television camera 6, an A/D converter 7, a display processor 8, an image display device 9, a compensation filter 10, a filter drive circuit 11, a collimator 12, a collimator drive circuit 13, a control circuit 19, and a display area detector 18.

A subject 1 is laid down on the upper face of the bed 2. The bed 2 is raised up or tilted to assume various positions such as a horizontal position, an oblique position and an upright position. The X-ray tube 3 emits an X-ray onto the subject 1 laid down on the bed 2. The X-ray irradiation is controlled by a control signal outputted from an X-ray controller 16 which will be described later. An image of the X-ray emitted from the X-ray tube 3 and transmitted through the subject 1 is incident upon the X-ray detector 4. The X-ray detector 4 converts the X-ray image to a visible light image. The X-ray detector 4 includes an X-ray image intensifier, for example. Furthermore, the X-ray tube 3 is disposed on the opposite side of the bed 2 from the X-ray detector 4. The X-ray tube 3 and the X-ray detector 4 are supported on opposite ends of the support 5 called C-arm, for example. The support 5 is controlled so as to conduct a movement such as rotation by a control signal outputted from a support controller 17 which will be described later.

The television camera 6 scans the visible light image converted and outputted by the X-ray detector 4 and outputs a video signal. The A/D converter 7 is supplied with the video signal outputted from the television camera 6. The A/D converter converts the video signal to a digital signal. The display processor 8 processes the digital signal supplied from the A/D converter 7 and converts image data thus processed to a video signal. The display processor 8 includes an image processor 14 and a display circuit 15. The image processor 14 conducts processing such as frequency emphasis processing (processing for amplifying a high-frequency component included in the video signal and emphasizing contours of the image) and subtraction processing (processing for subtracting an image obtained before injection of a contrast medium into a blood vessel from an image obtained after injection of the contrast medium and displaying only the image of the blood vessel) on the digital signal supplied from the A/D converter 7. A display area to be displayed on the image display device 9 is inputted to the display circuit 15 to select the display area by a console 20. The display circuit 15 extracts image data associated with the selected display area from image data supplied from the image processor 14 and converts the extracted image data to a video signal. The image display device 9 is supplied with the video signal from the display circuit 15 and displays the video signal as an image. For example, a television monitor is used as the image display device 9.

The compensation filter 10 functions to decrease the quantity of the X-ray irradiated upon a part of the subject and included in the X-ray emitted from the X-ray tube 3 toward the subject 1. For example, the compensation filter 10 is formed by a plurality of plate members including aluminum or copper. The compensation filter 10 is disposed so as to be movable parallel to a face of the X-ray tube 3 opposed to the subject 1. The control circuit 19 is supplied with image data processed by the image processor 14 in the display processor 8 as described below. On the basis of the image data, the control circuit 19 calculates control positions of the filter and collimator and controls the compensation filter 10 and the collimator 12 via the filter drive circuit 11 and the collimator drive circuit 13, respectively. The control circuit 19 sends control signals S1 and S2 based upon the result of calculation to the filter drive circuit 11 and the collimator drive circuit 13, respectively. The collimator 12 partially interrupts the X-ray emitted from the X-ray tube 3 toward the subject 1. The collimator 12 includes a plurality of plate members formed by an X-ray absorbing material such as lead. The collimator 12 is disposed so as to be movable between the output face of the X-ray tube 3 and the compensation filter 10. The control circuit 19 is supplied with image data processed by the image processor 14. The control circuit 19 functions to calculate the control position of the collimator and controls the collimator 12. Via the collimator drive circuit 13, the control circuit 19 sends a control signal S2 based upon the result of calculation to the collimator drive circuit 13.

In FIG. 6, the X-ray controller 16 is provided to control the operation of the X-ray tube 3. The X-ray controller 16 sets X-ray conditions such as tube voltage, tube current and exposure time. The support controller 17 is provided to control driving of the bed 2 and the support 5. The support controller 17 raises or tilts the bed 2 so as to attain a position such as a horizontal, oblique or upright position, and rotates the support 5 suitably. Thus, the support controller 17 exercises movement control. A combination of movements of the bed 2 and the support 5 allows positioning in a large number of positions in fluoroscopy and radiography.

In accordance with the present invention, the display area detector 18 is connected to the display circuit 15 included in the display processor 8 and a detection signal S3 of the display area detector 18 is sent to the control circuit 19. This display area detector 18 is supplied with a video signal from the display circuit 15 to detect the display area of an image displayed on the image display device 9. For example, the display area detector 18 detects an image signal of the display area in expansion or compression display and sends the image signal as the detection signal S3. By using both the image data processed by the image processor 14 and the image signal of the display area of the image display device 9 detected by the display area detector 18, therefore, the control circuit 19 calculates the control position of the filter and controls the position of the compensation filter 10.

Figure 7:
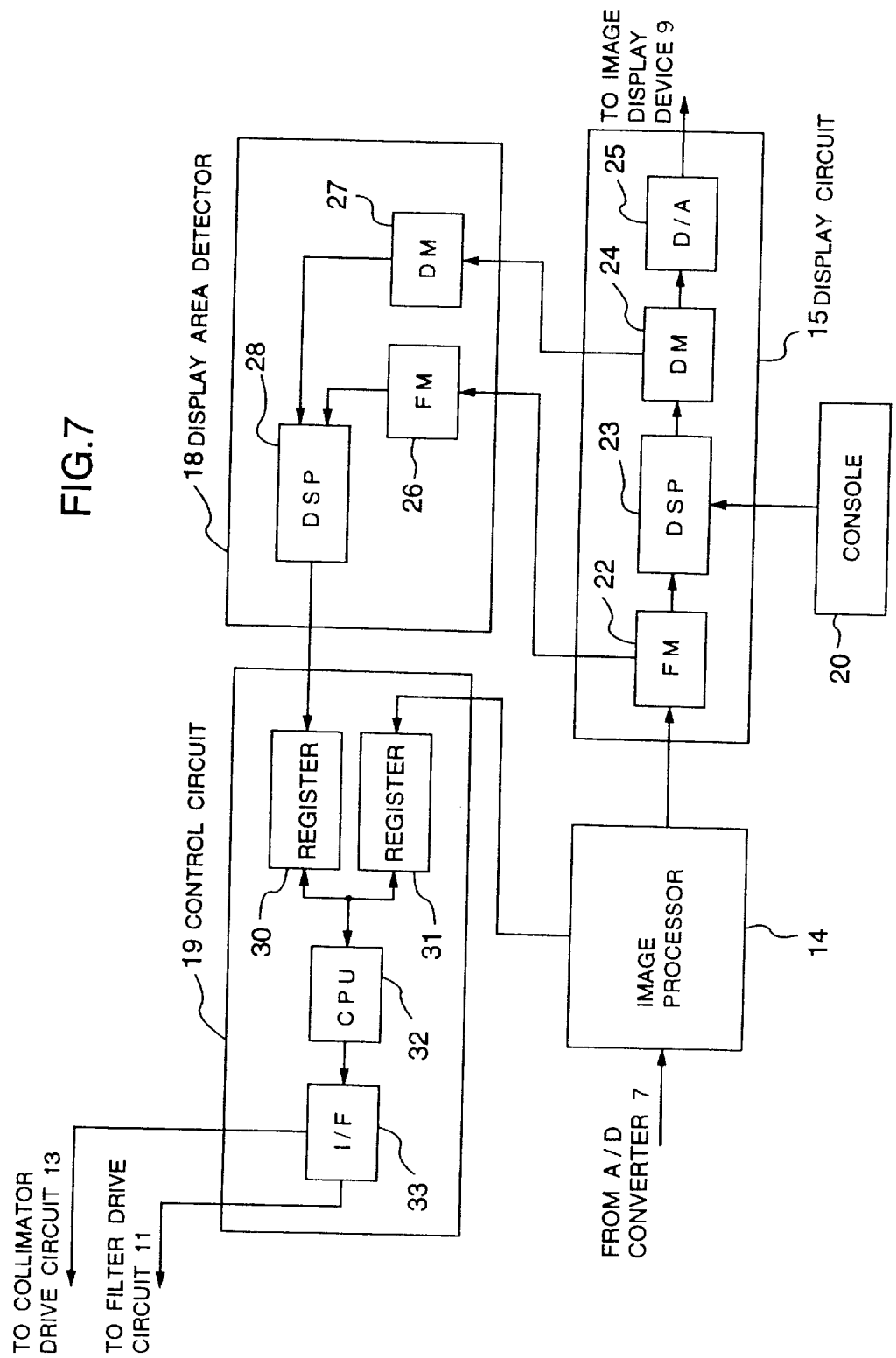
FIG. 7 is a block diagram showing a detailed configuration of a principal part of FIG. 6.

With reference to FIG. 7, mutual relations of the image processor 14, the display circuit 15, the control circuit 19 and the display area detector 18 and internal configurations of them will now be described in more detail.

With reference to FIG. 7, the digital signal supplied from the A/D converter 7 is subjected to image data processing in the image processor 14 and then stored in a field memory 22 included in the display circuit 15. Therefore, image data stored in this field memory 22 are data of the entire image picked up by the television camera 6. On the basis of a display area specifying command supplied by an operator via the console 20, a digital signal processor 23 generates image data of the specified display area from image data stored in the field memory 22 by using a conventionally known method and stores the generated image data into a display memory 24. A D/A converter 25 successively reads out image data stored in the display memory 24, performs D/A conversion on the image data thus read out, and transmits the D/A converted image data to the image display device 9 as a video signal.

A field memory 26 and a display memory 27 included in the display area detector 18 regularly take in image data stored in the field memory 22 and the display memory 24 included in the display circuit 8, respectively. A digital signal processor 28 compares and collates image data stored in the field memory 26 with image data stored in the display memory 27, calculates data representing coordinates of the display area, and stores the calculated data into a register 30 included in the control circuit 19. Another register 31 stores image data successively subjected to signal processing in the image processor 14.

Figure 8:
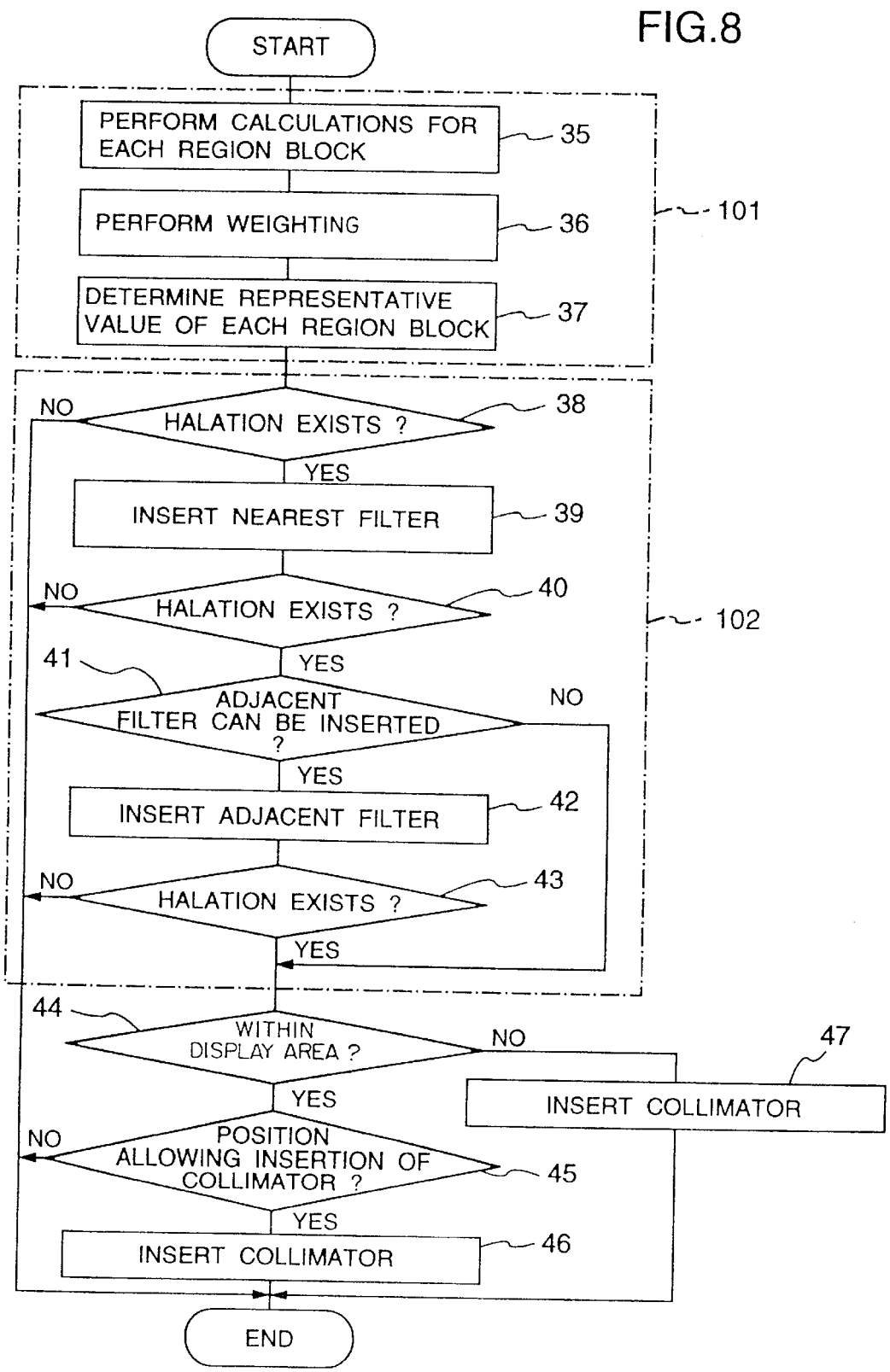
FIG. 8 is a flow chart showing an example of operation in the embodiment illustrated in FIGS. 6 and 7.

On the basis of data stored in the registers 30 and 31, a CPU (central processing unit) 32 operates according to a flow chart shown in FIG. 8. The CPU 32 sends control signals to the filter drive circuit 11 and the collimator drive circuit 13 via an interface 33 to control positions of the compensation filter 10 and the collimator 12, respectively. The concept of this control operation will hereafter be described.

Figure 4:
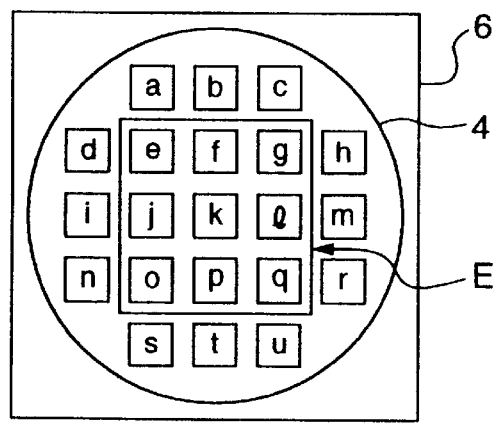
FIGS. 4 and 5 are diagrams showing the range of a display image area of a display device in the apparatus shown in FIG. 2.
Figure 5:
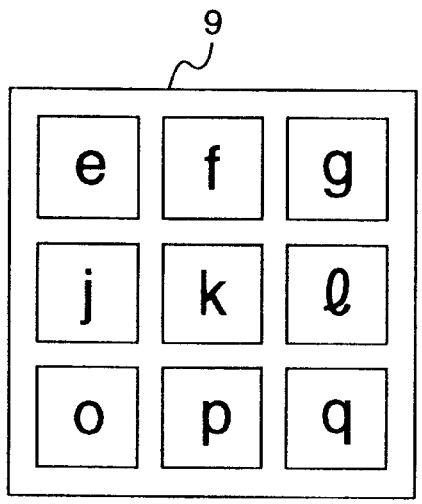
Figure 9:
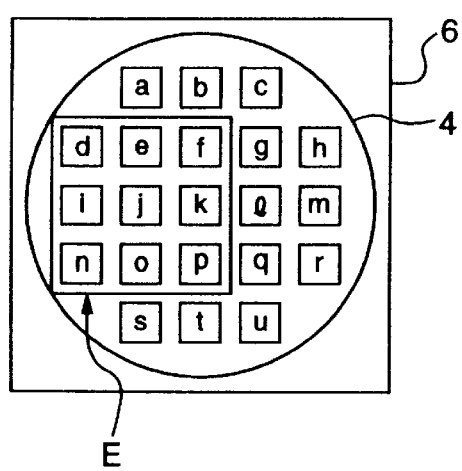
FIGS. 9 through 13 are diagrams for explaining functions of the present invention.
Figure 11:
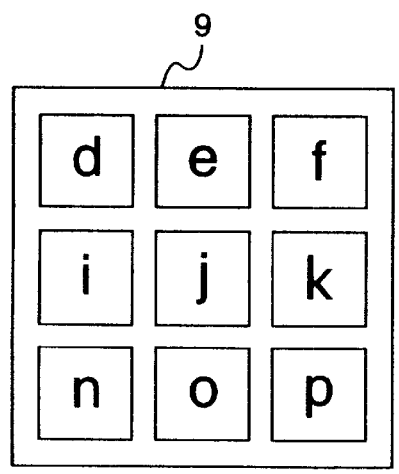

In FIG. 9, a picked-up image area for expansion display included in the output image region of the X-ray detector 4 is represented by a square region E in the same way as FIG. 4. As an example, the case where region blocks d, e, f, i, j, k, n, o and p included in the region E are expanded and displayed is illustrated. FIG. 11 shows an expanded display of region blocks d, e, f, i, j, k, n, o and p of a display image area on the image display device 9.

Figure 12:
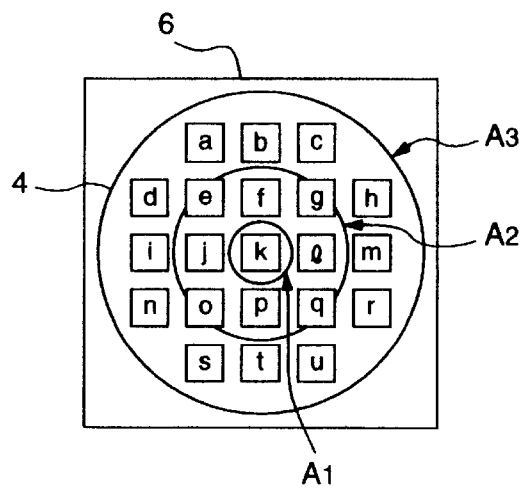
Figure 13:
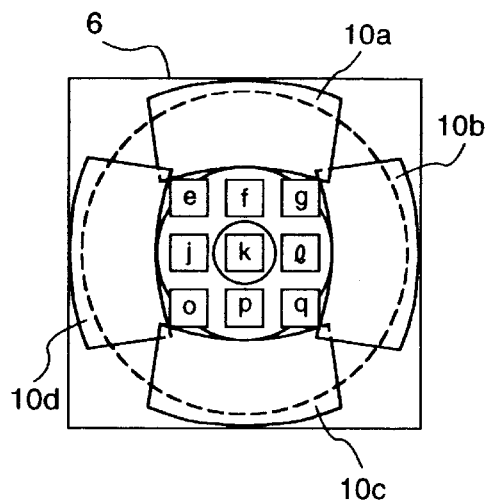

FIG. 12 shows the case where region blocks of the whole image are weighted and displayed in the output image region of the X-ray detector 4. That is to say, a circular output image region is divided into three concentric circle regions A1, A2 and A3, for example. The region block k located at the center of the innermost region A1 is provided with the largest weight. Each of the region blocks e, f, g, j, l, o, p and q included in the second region A2 located outside of the region A1 is provided with the second largest weight. Furthermore, each of the region blocks a, b, c, d, h, i, m, n, r, s, t and u included in the third region A3 located outside of the second region A2 is provided with the third largest weight. Thereby, the innermost region Al is given priority. As shown in FIG. 13, for example, four filter blades 10*a* through 10*d* of the compensation filter 10 according to the intermediate technique shown in FIG. 2 can move from the periphery toward the center. And the four filter blades 10*a* through 10*d* are set so as to limit the irradiation X-ray on the outside of the second region A2.

Figure 10:
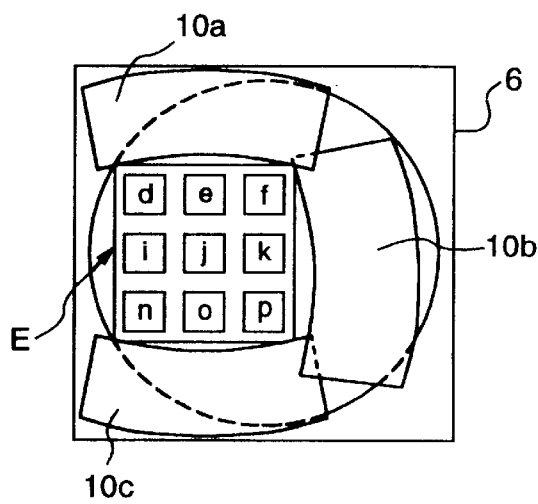

However, weighting of display regions and control of the compensation filter 10 in the example of the technique shown in FIGS. 12 and 13 have the following drawback. In case the square region E shown in FIG. 9 is desired to be expanded and displayed, the difference in weight between the region blocks i and k is large and suitable control of the compensation filter 10 cannot be expected if weighting as shown in FIG. 12 is used. In case of FIG. 9, therefore, the region block j located at the center of the square region E should be provided with the largest weight, and region blocks d, e, f, i, k, n, o and p located outside the region block j should be provided with the second largest weight. Thereby, the region block j located at the center of the square region E is given priority. As shown in FIG. 10, for example, four filter blades 10*a* through 10*d* (where 10*d* is not illustrated) of the compensation filter 10 according to the present invention shown in FIG. 6 can move from the periphery toward the center of the square region E. And the four filter blades 10*a* through 10*d* are set so as to limit the irradiation X-ray on the outside of the region E. In case the expansion region E shown in FIG. 9 has moved to another location, the above described operation should be executed again for a new region block located at the destination of the movement. Owing to such operation, control of the compensation filter 10 suitable for the expanded and displayed image can be exercised.

Operation of the CPU 32 included in the control circuit 19 in the embodiment of the present invention heretofore described will now be described by referring to a flow chart shown in FIG. 8.

In FIG. 8, processing begins at "START". At step 35, image data of respective pixels stored in the register 31 are read out for all region blocks a through u shown in FIG. 9, and the arithmetic mean, maximum and minimum of magnitude values of all pixel data are calculated for each of the region blocks and stored in a memory included in the CPU 32.

At step 36, coordinates of a display area to be subjected to expansion display are read out from the register 30 and a region block j located at the center of the display area is determined. This block j is provided with the largest weight, and region blocks located outside the region block j are provided with the second largest weight. Region blocks located outside region blocks provided with the second largest weight are provided with the third largest weight. The larger a weight a region has, the harder a filter makes it.

At step 37, a representative value of each region block is determined on the basis of the value calculated at step 35. As this representative value, the arithmetic mean value is typically used. Alternatively, the maximum value may be used. At step 38, the representative value of each region block is compared with a predetermined value giving a reference of halation. Depending upon whether the representative value exceeds the predetermined value, it is determined whether halation exists. When halation exists, it is determined which coordinate values the region block wherein halation exists has.

If it is found at step 38 that no halation exists for every region block, processing proceeds to "END." If halation exists, however, a filter located nearest to a coordinate position of a region block involving halation is inserted as far as that position at step 39. It is checked at step 40 whether halation has disappeared as a result. If halation is judged to have disappeared at step 40, processing proceeds to "END." If halation still exists, it is determined at step 41 whether an adjacent filter can be inserted as far as the position of the halation. If it is possible, that adjacent filter is inserted at step 42. Furthermore, it is checked at step 43 whether halation has disappeared. If halation is judged to have disappeared at step 43, processing proceeds to "END." If halation still exists, processing proceeds to step 44. It is determined at step 44 whether the region block involving halation is within the display area.

Also, when it is determined at step 41 that the adjacent filter cannot be inserted, processing skips to step 44.

When the region block involving halation is judged at step 44 to be on the outside of the display area, the display picture is not affected even if the X-ray is interrupted and hence the collimator is inserted as far as that region block at step 47 and processing proceeds to "END." When the region block involving halation is judged at step 44 to be within the display area, it is determined at step 45 whether the region block involving halation is located in such a position that a bad influence is not exerted upon the displayed image even if the collimator is inserted. If the result of judgment is "YES," the collimator is inserted as far as that region block and processing proceeds to "END." If the result of judgment is "NO," there is no further way to cope with the halation and hence processing directly proceeds to "END."

Operation of the circuit configuration shown in FIG. 6 has heretofore been described by referring to the flow chart of FIG. 8. Another example of operation will now be described by referring to FIG. 14. A region calculation processing step 101 and a filter insertion processing step 102 shown in FIG. 14 correspond to steps 35 through 37 and steps 38 through 43 shown in FIG. 8, respectively.

Figure 14:
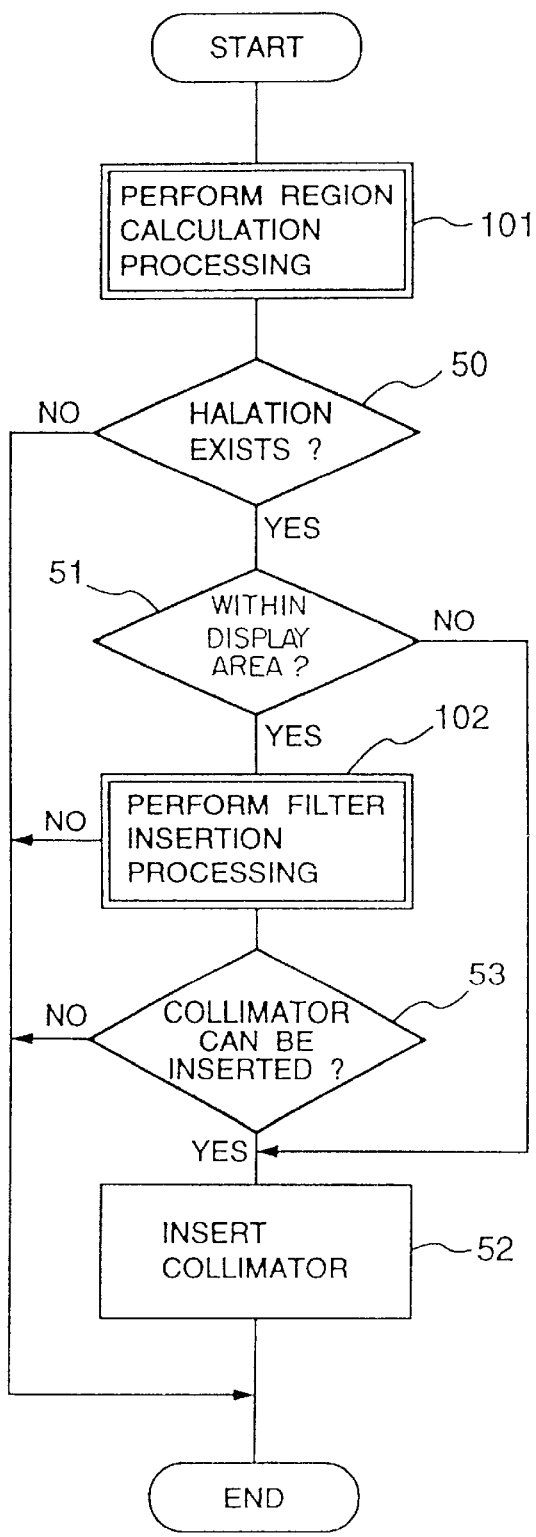
FIG. 14 is a flow chart showing another example of operation in the embodiment illustrated in FIGS. 6 and 7.

With reference to FIG. 14, processing begins at "START." started. At step 101, the same operation as steps 35 through 37 of FIG. 8 is conducted. Processing then proceeds to step 50. At step 50, it is determined whether halation exists. If the result of judgment at step 50 is "NO," processing proceeds directly to "END." If the result of judgment at step 50 is "YES," it is determined at step 51 whether the position of halation is within the display area. If the result of judgment at step 51 is "NO," the position of halation is located outside the display area and hence the X-ray is desired to be interrupted. At step 52, therefore, a collimator is inserted as far as the existence position of halation and processing proceeds to "END."

If the result of judgment at step 51 is "YES," filter insertion processing is conducted at step 102. This processing is identical with steps 38–43 of FIG. 8. If the result of judgment at step 38, 40 or 43 included in this processing is "NO," processing proceeds to "END." If halation still exists, it is determined at step 53 whether the collimator can be inserted as far as the position of the collimator. If the result of judgment at step 53 is "YES," the collimator is inserted at step 52 and processing proceeds to "END."If the result of judgment at step 53 is "NO," processing proceeds directly to "END."

In case the expansion display region E shown in FIG. 9 is small, weights of region blocks d, e, f, i, j, k, n, o and p in the region E may have the same magnitude. In the embodiment of FIG. 6, information supplied from the image processor 14 included in the display processor 8 and information supplied from the display area detector 18 are inputted to the control circuit 19 to control the compensation filter 10. However, this is not restrictive. Instead of providing the display area detector 18 and the control circuit 19, weighting of region blocks and calculation of the representative values in all display images including the expansion image may be executed in the display circuit 15 included in the display processor 8.

Figure 15:
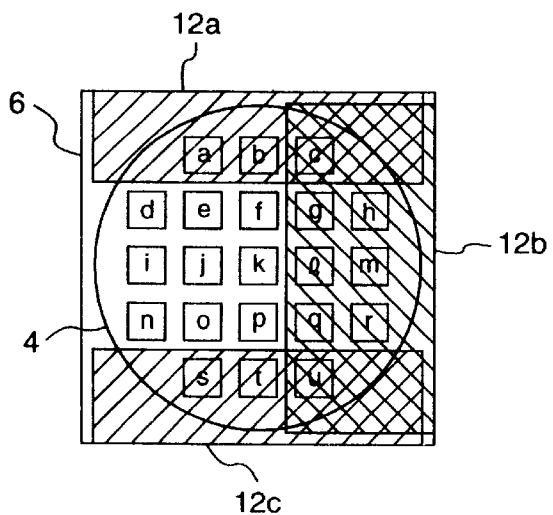
FIG. 15 is a diagram for explaining another example of operation of the present invention.

The concept of another embodiment of the present invention will now be described by referring to FIG. 15. FIG. 15 shows the case where region blocks d, e, f, i, j, k, n, o and p included in the output image region of the X-ray detector 4 are expanded and displayed in the same way as in FIG. 9. In this case, four X-ray blocking members 12a, 12b, 12c and 12d (where 12d is not illustrated) of the collimator 12 are inserted from the periphery by control operation of the collimator drive circuit 13, and the region outside of the region blocks d, e, f, i, o, k, n, o and p is completely covered to interrupt the irradiation X-ray. At this time, the compensation filter 10 is also moved simultaneously by control operation of the filter drive circuit 11. Positions of the filter blades 10a through 10c are thus set as shown in FIG. 10. By the way, even if only the X-ray interruption performed by position control of the collimator 12 is used, there is an effect of preventing X-ray exposure. Control of the compensation filter 10 is exercised for the purpose of preventing halation in the display area.

Figure 16:
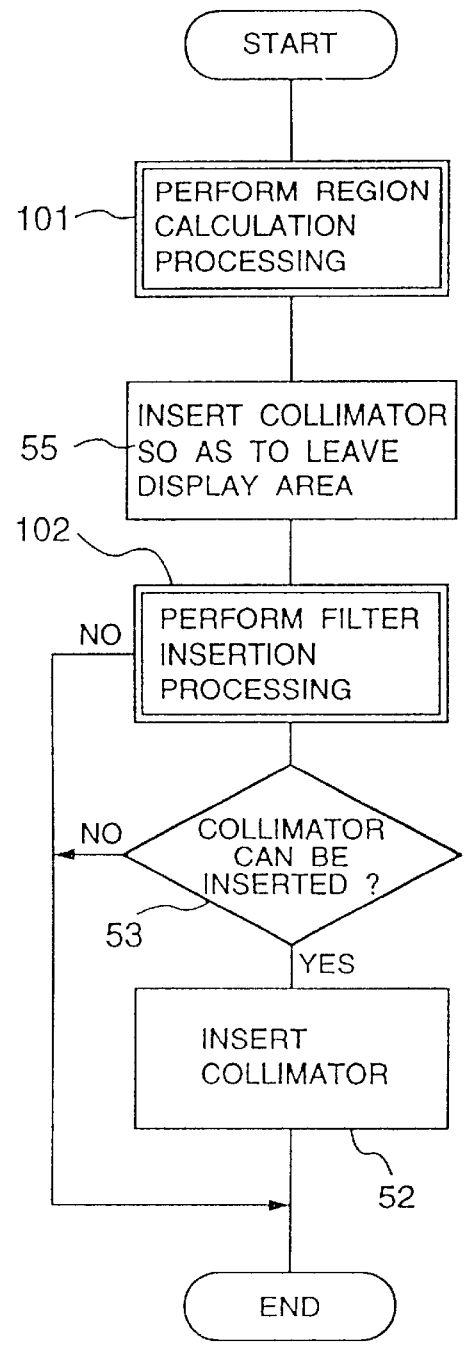
FIG. 16 is a flow chart showing another example of operation of the present invention.

This embodiment is implemented by the circuit configuration shown in FIGS. 6 and 7. The CPU 32 included in the circuit configuration executes operation of this embodiment according to a flow shown in FIG. 16. In FIG. 16, steps corresponding to those of FIG. 14 are denoted by like numerals.

With reference to FIG. 16, region calculation processing similar to that described before is first conducted at step 101. Then, at step 55, the collimator is inserted so as to leave the display area as shown in FIG. 15. Thus, the subject is not exposed to unnecessary X-ray irradication. At step 102, the position of the compensation filter 10 is controlled in processing for eliminating halation existing in the display area similar to that described before. Thereafter, operation completely identical with that of FIG. 14 is conducted.

In the above described embodiment, the display area detector 18 takes in an image signal from the display circuit 15 included in the display processor 8. The present invention is not limited to this. Alternatively, a signal may be taken in directly from the image processor 14 which is also included in the display processor 8.

Owing to the configuration of the present invention heretofore described, an image signal from a display processor is inputted to a display area detector connected to the display processor. The display area of the image is detected in the display area detector. The image signal of the detected display area is sent to a filter drive circuit. Owing to operation of this filter drive circuit, a compensation filter and a collimator of an X-ray tube can be controlled by using the image signal of the display area as well. Therefore, even if collected images are expanded and displayed, for example, therefore, positions of the compensation filter and the collimator can be controlled and set so as to optimize the image of the area of expansion display.

Furthermore, the image signal of the display area detected by the display area detector is sent to the filter drive circuit and the collimator drive circuit. The compensation filter is controlled by operation of the filter drive circuit, and the collimator is controlled by operation of the collimator drive circuit. The X-ray irradiation of the portion except the display area can thus be interrupted. As a result, the compensation filter and the collimator can be controlled optimally. In this case, undesired exposure of the suject to the X-ray can be prevented more efficiently.

What is claimed is:

1. An X-ray image display apparatus comprising:

X-ray image detecting means for transmitting an X-ray through a subject and detecting an X-ray image of the subject;

video signal processing means for converting the X-ray image detected by the X-ray image detecting means to a video signal and performing image processing on the video signal to generate X-ray image data;

an input device for specifying an entire display area to be displayed in the X-ray image detected by the X-ray image detecting means;

a display circuit for extracting display image data corresponding to the entire display area specified by the input device based on the X-ray image data generated by the video signal processing means;

a display device for converting the display image data extracted by the display circuit to a video signal and displaying the video signal as an image corresponding to the entire display area specified by the input device;

a collimator, having an X-ray transmitting aperture, for interrupting an X-ray except within the X-ray transmitting aperture of the collimator;

collimator drive means for driving the collimator;

display area detecting means for generating display area data representing the entire display area specified by the input device based on the X-ray image data and the display image data; and a controller for outputting a control signal to the collimator drive means to control a position of the collimator and a size of the X-ray transmitting aperture of the collimator based on the display area data generated by the display area detecting means such that the collimator interrupts the X-ray from being transmitted through any portion of the subject substantially other than a portion of the subject corresponding to the entire display area specified by the input device.

2. An X-ray image display apparatus according to claim 1, wherein the controller includes:

means for detecting predetermined data in X-ray image data corresponding to the entire display area specified by the input device; and means for outputting a control signal to the collimator drive means to control the position of the collimator to eliminate the predetermined data based on the display area data generated by the display area detecting means.

3. An X-ray image display apparatus according to claim 1, wherein the controller includes means for detecting predetermined data in X-ray image data corresponding to the entire display area specified by the input device.

4. An X-ray image display apparatus according to claim 1, wherein the display circuit includes:
   a field memory for storing the X-ray image data generated by the video signal processing means;
   a digital signal processor for reading out the X-ray image data stored in the field memory and extracting display image data corresponding to the entire display area specified by the input device from the X-ray image data read out from the field memory; and
   a display memory for storing the display image data extracted by the digital signal processor.

5. An X-ray image display apparatus according to claim 1, wherein the display area detecting means includes:
   a field memory for storing the X-ray image data generated by the video signal processing means;
   a display memory for storing the display image data extracted by the display circuit; and
   means for generating the display area data based on the X-ray image data stored in the field memory and the display image data stored in the display memory.

6. An X-ray image display apparatus according to claim 1, wherein the controller includes:
   a first register for storing the display area data generated by the display area detecting means;
   a second register for storing the X-ray image data generated by the video signal processing means; and
   a calculation processing device for generating the control signal which is outputted to the collimator drive means based on the display area data stored in the first register.

7. An X-ray image display apparatus according to claim 1, wherein the display circuit includes means for converting the extracted display image data corresponding to the entire display area specified by the input device to converted display image data for producing a display image having a size substantially equal to a size of an entire display area of the display device.

8. An X-ray image display apparatus according to claim 1, wherein a size of the entire display area specified by the input device is different from a size of the X-ray image detected by the X-ray image detecting means.

9. An X-ray image display apparatus comprising:
   X-ray image detecting means for transmitting an X-ray through a subject and detecting an X-ray image of the subject;
   video signal processing means for converting the X-ray image detected by the X-ray image detecting means to a video signal and performing image processing on the video signal to generate X-ray image data;
   an input device for specifying a display area to be displayed in the X-ray image detected by the X-ray image detecting means;
   a display circuit for generating display image data corresponding to the display area specified by the input device based on the X-ray image data generated by the video signal processing means;
   a display device for converting the display image data generated by the display circuit to a video signal and displaying the video signal as an image;
   a collimator, having an X-ray transmitting aperture, for interrupting an X-ray except within the X-ray transmitting aperture of the collimator;
   collimator drive means for driving the collimator;
   display area detecting means for generating display area data representing the display area based on the X-ray image data and the display image data; and
   a controller for outputting a control signal to the collimator drive means to control a position of the collimator and a size of the X-ray transmitting aperture of the collimator based on the display area data generated by the display area detecting means such that the collimator interrupts the X-ray from being transmitted through any portion of the subject substantially other than a portion of the subject corresponding to the display area specified by the input device;
   wherein the controller includes:
      a first register for storing the display area data generated by the display area detecting means;
      a second register for storing the X-ray image data generated by the video signal processing means; and
      a calculation processing device for generating the control signal which is outputted to the collimator drive means based on the display area data stored in the first register; and
   wherein the calculation processing device includes:
      means for dividing a detection region of the X-ray image into a plurality of region blocks and determining a representative value of X-ray image data included in each region block;
      halation detecting means for comparing the representative value of each region block with a predetermined value and determining whether halation exists based on a result of the comparing; and
      means, responsive to detection of existence of halation by the halation detecting means, for outputting a control signal to the collimator drive means to control the position of the collimator to eliminate the halation.

10. An X-ray image display apparatus comprising:
    X-ray image detecting means for transmitting an X-ray through a subject and detecting an X-ray image of the subject;
    video signal processing means for converting the X-ray image detected by the X-ray image detecting means to a video signal and performing image processing on the video signal to generate X-ray image data;
    an input device for specifying a display area to be displayed in the X-ray image detected by the X-ray image detecting means;
    a display circuit for generating display image data corresponding to the display area specified by the input device based on the X-ray image data generated by the video signal processing means;
    a display device for converting the display image data generated by the display circuit to a video signal and displaying the video signal as an image;
    a collimator, having an X-ray transmitting aperture, for interrupting an X-ray except within the X-ray transmitting aperture of the collimator;
    collimator drive means for driving the collimator;
    display area detecting means for generating display area data representing the display area based on the X-ray image data and the display image data; and
    a controller for outputting a control signal to the collimator drive means to control a position of the collimator and a size of the X-ray transmitting aperture of the collimator based on the display area data generated by the display area detecting means such that the collimator interrupts the X-ray from being transmitted through any portion of the subject substantially other than a portion of the subject corresponding to the display area specified by the input device;

wherein the display circuit includes means for detecting predetermined data in X-ray image data corresponding to the display area specified by the input device; and wherein the predetermined data is data representing halation.

11. An X-ray image display apparatus comprising:

X-ray image detecting means for transmitting an X-ray through a subject and detecting an X-ray image of the subject;

video signal processing means for converting the X-ray image detected by the X-ray image detecting means to a video signal and performing image processing on the video signal to generate X-ray image data;

an input device for specifying a display area to be displayed in the X-ray image detected by the X-ray image detecting means;

a display circuit for generating display image data corresponding to the display area specified by the input device based on the X-ray image data generated by the video signal processing means;

a display device for converting the display image data generated by the display circuit to a video signal and displaying the video signal as an image;

a collimator, having an X-ray transmitting aperture, for interrupting an X-ray except within the X-ray transmitting aperture of the collimator;

collimator drive means for driving the collimator;

display area detecting means for generating display area data representing the display area based on the X-ray image data and the display image data; and a controller for outputting a control signal to the collimator drive means to control a position of the collimator and a size of the X-ray transmitting aperture of the collimator based on the display area data generated by the display area detecting means such that the collimator interrupts the X-ray from being transmitted through any portion of the subject substantially other than a portion of the subject corresponding to the display area specified by the input device;

wherein the controller includes:
means for assigning different weights to portions of the display area specified by the input device such that a highest weight is assigned to a central portion of the display area specified by the input device and a lowest weight is assigned to a peripheral portion of the display area specified by the input device.

12. An X-ray image display apparatus comprising:

an X-ray source which transmits an X-ray through a subject;

an X-ray detector which detects the X-ray transmitted through the subject and produces an X-ray image of the subject from the detected X-ray;

a video signal generator which converts the X-ray image into an X-ray image video signal;

a video signal processor which generates X-ray image data from the X-ray image video signal;

an input device which specifies a portion of the X-ray image as an entire display area to be displayed on an entire display area of a display device, the specified portion of the X-ray image being smaller than an entire area of the X-ray image;

a display circuit which extracts X-ray image data corresponding to the portion of the X-ray image specified by the input device from the X-ray image data generated by the video signal processor, expands the extracted X-ray image data to produce expanded X-ray image data corresponding to the entire display area of the display device, and converts the expanded X-ray image data into a display video signal;

a display device which displays the display video signal as an expanded X-ray image on the entire display area of the display device;

a collimator, having a controllable position and an X-ray transmitting aperture having a controllable size, which interrupts an X-ray except within the X-ray transmitting aperture of the collimator;

a collimator drive circuit which controls the position of the collimator and the size of the X-ray transmitting aperture of the collimator in response to a control signal;

a display area detector which generates display area data representing the portion of the X-ray image specified as a display area by the input device based on the X-ray image data and one of (1) the extracted X-ray image data and (2) the expanded X-ray image data; and a controller which generates a control signal for the collimator drive circuit based on the display area data generated by the display area detector and outputs the control signal to the collimator drive circuit, the control signal being effective to cause the collimator drive circuit to control the position of the collimator and the size of the X-ray transmitting aperture of the collimator so that the collimator interrupts the X-ray from being transmitted through any portion of the subject substantially other than a portion of the subject corresponding to the portion of the X-ray image specified by the input device.

13. An X-ray image display apparatus comprising:

X-ray image detecting means for transmitting an X-ray through a subject and detecting an X-ray image of the subject;

video signal processing means for converting the X-ray image detected by the X-ray image detecting means to a video signal and performing image processing on the video signal to generate X-ray image data;

an input device for specifying an entire display area to be displayed in the X-ray image detected by the X-ray image detecting means;

a display circuit for extracting display image data corresponding to the entire display area specified by the input device based on the X-ray image data generated by the video signal processing means;

a display device for converting the display image data extracted by the display circuit to a video signal and displaying the video signal as an image corresponding to the entire display area specified by the input device;

a collimator, having an X-ray transmitting aperture, which interrupts an X-ray except within the X-ray transmitting aperture of the collimator;

collimator drive means for driving the collimator;

a filter which decreases an exposure dose of the subject to the X-ray without interrupting the X-ray;

filter drive means for driving the filter; and a controller for outputting a control signal to the collimator drive means to control a position of the collimator and a size of the X-ray transmitting aperture of the collimator based on the entire display area specified by the input device such that the collimator interrupts the X-ray from being transmitted through any portion of the subject substantially other than a portion of the subject corresponding to the entire display area specified by the input device, and subsequently outputting a control signal to the filter drive means to control a position of the filter based on the entire display area specified by the input device.

14. An X-ray image display apparatus according to claim 13, wherein a size of the entire display area specified by the input device is different from a size of the X-ray image detected by the X-ray image detecting means.

15. An X-ray image display apparatus according to claim 13, wherein the display circuit includes means for converting the extracted display image data corresponding to the entire display area specified by the input device to converted display image data for producing a display image having a size substantially equal to a size of an entire display area of the display device.

16. An X-ray image display apparatus comprising:

X-ray image detecting means for transmitting an X-ray through a subject and detecting an X-ray image of the subject;

video signal processing means for converting the X-ray image detected by the X-ray image detecting means to a video signal and performing image processing on the video signal to generate X-ray image data;

an input device for specifying a display area to be displayed in the X-ray image detected by the X-ray image detecting means;

a display circuit for generating display image data corresponding to the display area specified by the input device based on the X-ray image data generated by the video signal processing means;

a display device for converting the display image data generated by the display circuit to a video signal and displaying the video signal as an image;

a collimator, having an X-ray transmitting aperture, for interrupting an X-ray except within the X-ray transmitting aperture of the collimator;

collimator drive means for driving the collimator;

display area detecting means for generating display area data representing the display area based on the X-ray image data and the display image data; and a controller for outputting a control signal to the collimator drive means to control a position of the collimator and a size of the X-ray transmitting aperture of the collimator based on the display area data generated by the display area detecting means such that the collimator interrupts the X-ray from being transmitted through any portion of the subject substantially other than a portion of the subject corresponding to the display area specified by the input device;

wherein the controller includes:
means for assigning different weights to portions of the display area specified by the input device such that a highest weight is assigned to a central portion of the display area specified by the input device and a lowest weight is assigned to a peripheral portion of the display area specified by the input device; and means for generating the control signal which is outputted to the collimator drive means based on the display area data generated by the display area detecting means and the different weights assigned to portions of the display area specified by the input device such that the higher a weight a particular portion of the display area specified by the input device has, the less likely it is that the collimator will be positioned at a position corresponding to the particular portion of the display area specified by the input device.

17. An X-ray image display apparatus comprising:

X-ray image detecting means for transmitting an X-ray through a subject and detecting an X-ray image of the subject;

video signal processing means for converting the X-ray image detected by the X-ray image detecting means to a video signal and performing image processing on the video signal to generate X-ray image data;

an input device for specifying a display area to be displayed in the X-ray image detected by the X-ray image detecting means;

a display circuit for generating display image data corresponding to the display area specified by the input device based on the X-ray image data generated by the video signal processing means;

a display device for converting the display image data generated by the display circuit to a video signal and displaying the video signal as an image;

a collimator, having an X-ray transmitting aperture, for interrupting an X-ray except within the X-ray transmitting aperture of the collimator;

collimator drive means for driving the collimator;

display area detecting means for generating display area data representing the display area based on the X-ray image data and the display image data; and a controller for outputting a control signal to the collimator drive means to control a position of the collimator and a size of the X-ray transmitting aperture of the collimator based on the display area data generated by the display area detecting means such that the collimator interrupts the X-ray from being transmitted through any portion of the subject substantially other than a portion of the subject corresponding to the display area specified by the input device;

wherein the controller includes:
means for detecting predetermined data in X-ray image data corresponding to the display area specified by the input device; and
means for outputting a control signal to the collimator drive means to control the position of the collimator to eliminate the predetermined data based on the display area data generated by the display area detecting means;

wherein the predetermined data is data representing halation; and wherein the means for outputting a control signal outputs a control signal to the collimator drive means to control the position of the collimator to eliminate the data representing halation based on the display area data generated by the display area detecting means.

* * * * *